United States Patent [19]
Nakanishi et al.

[11] Patent Number: 5,340,352
[45] Date of Patent: Aug. 23, 1994

[54] FIGURE ADJUSTING PAD AND PROCESS FOR MANUFACTURING SAME

[75] Inventors: Motoyasu Nakanishi; Masaaki Amano, both of Shizuoka, Japan

[73] Assignee: Kabushiki Kaisha Sigel, Tokyo, Japan

[21] Appl. No.: 889,371

[22] Filed: May 28, 1992

[30] Foreign Application Priority Data

May 30, 1991 [JP] Japan .................. 3-228132
Apr. 17, 1992 [JP] Japan .................. 4-125731

[51] Int. Cl.$^5$ .......................................... A41C 3/14
[52] U.S. Cl. .......................................... 450/57; 2/267;
2/243.1; 264/49; 450/30; 450/31; 450/32;
450/55; 623/7; 623/8
[58] Field of Search .............. 2/267, 268, 275, 22,
2/23, 24; 112/418, 419; 264/49; 450/30, 31, 32,
39, 40, 53, 54, 55, 56, 57; 623/7, 8

[56] References Cited

U.S. PATENT DOCUMENTS

| | | | |
|---|---|---|---|
| 2,526,808 | 10/1950 | Cohen | 2/268 |
| 2,727,278 | 12/1955 | Thompson | 450/39 X |
| 3,050,734 | 8/1962 | Dopyera | 2/268 |
| 3,266,495 | 8/1966 | Sachs | 450/55 |
| 3,801,420 | 4/1974 | Anderson | 112/419 X |
| 4,090,010 | 5/1978 | Warwicker et al. | 264/49 X |
| 4,212,839 | 7/1980 | Funahashi | 264/49 X |
| 4,380,569 | 4/1983 | Shaw | 450/54 |
| 4,566,458 | 1/1986 | Weinberg | 450/54 |
| 4,795,399 | 1/1989 | Davis | 2/268 X |
| 5,105,473 | 4/1992 | Valtakari | 2/267 X |
| 5,165,113 | 11/1992 | Hyams et al. | 2/268 |

FOREIGN PATENT DOCUMENTS

1522388 11/1989 Australia .................. 623/8

*Primary Examiner*—Clifford D. Crowder
*Assistant Examiner*—Jeanette E. Chapman
*Attorney, Agent, or Firm*—Wenderoth, Lind & Ponack

[57] ABSTRACT

A figure adjusting pad is capable of permitting a periphery of the pad to exhibit satisfactory shape retention without any independent core. The pad includes a silicone gel element formed therein with perforations and a stretchable fabric arranged for covering the silicone gel element and is trimmed. The perforations of the silicone gel element are formed by traces defined by elution of particles incorporated in a silicone gel stock solution for the silicone gel element. The trimmed portion includes the silicone gel element and is double-sewn together with the silicone gel element.

26 Claims, 9 Drawing Sheets

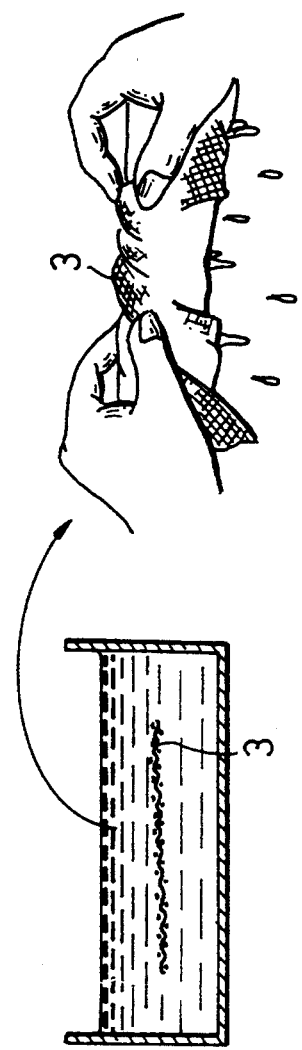
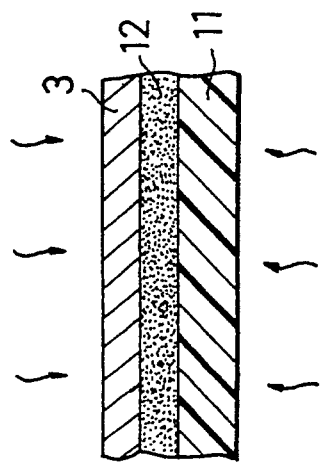
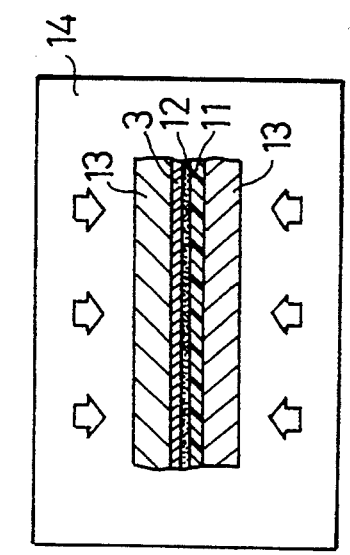
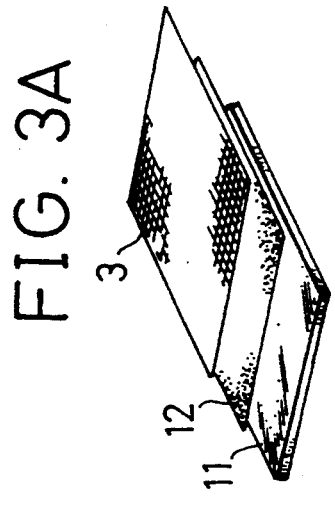
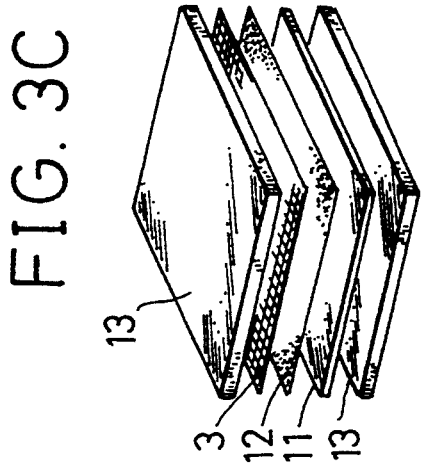
FIG. 3A
FIG. 3B
FIG. 3C
FIG. 3D
FIG. 3E

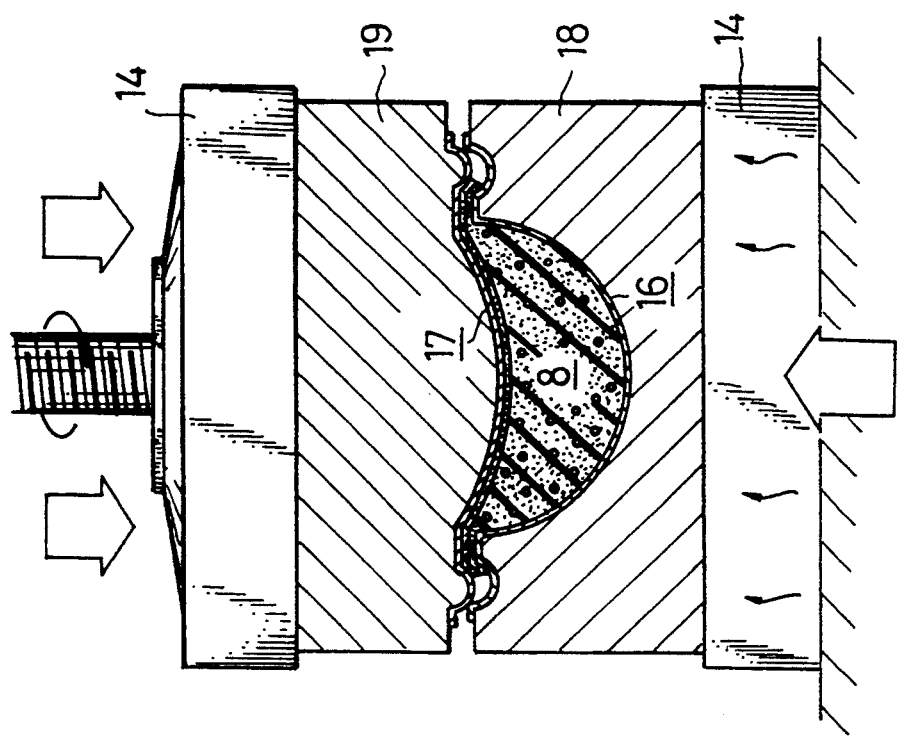
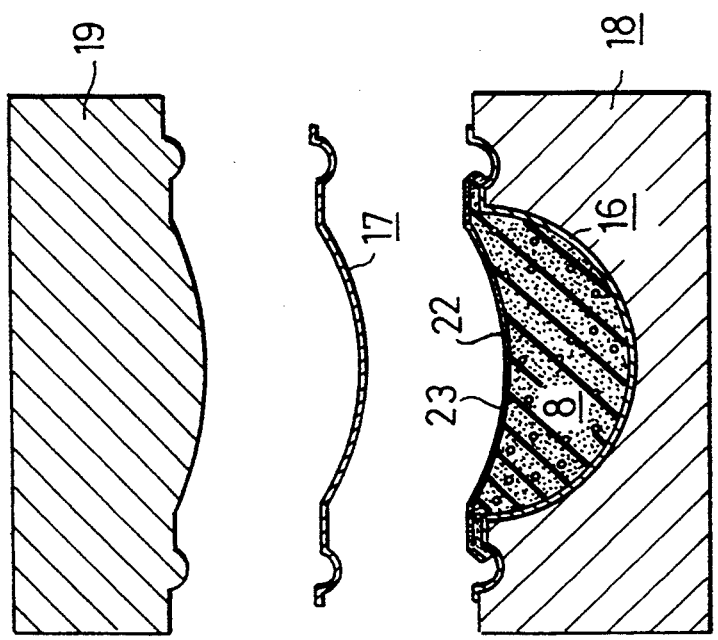

FIGURE ADJUSTING PAD AND PROCESS FOR MANUFACTURING SAME

BACKGROUND OF THE INVENTION

This invention relates to a figure retaining or adjusting pad and a process for manufacturing the same, and more particularly to a pad for adjusting a figure of, for example, a woman and a process for manufacturing the same.

When the breast of a woman has been excised by operation for, for example, mastitis or the like, a figure or breast adjusting pad made in conformity to the breast is often substituted therefor. Thus, because the figure adjusting pad is substituted for a part of the body, it is desired to exhibit properties similar to the body. Therefore, it is required to have flexibility, elasticity, shape-retention, touch and strength in conformity to the body. Also, the figure adjusting pad is typically fitted directly to the bare skin, so that it is required to exhibit satisfactory air-permeability and possess aesthetic properties and quality sufficient to act as a part of a lingerie.

In view of the foregoing, a pad formed of a gel-like material formed with perforations comprising open cells is proposed, as disclosed in Japanese Utility Model Publication No. 40728/1986. Unfortunately, the pad proposed is made of oily or water-containing gel material, so that a surface thereof is sticky. Thus, the conventional pad properties are deteriorated with respect to touch (or feel) in surface strength and shape-retention. In order to avoid such problems, the gel-like material is fully sealingly covered with a plastic film or the like. However, this fails to provide sufficient adhesion between the gel-like material of the pad and plastic film, resulting in peeling of the material from the plastic film, as well as movement and deformation of the gel-like material in the film and wrinkling of the film. Also, the conventional pad fails to exhibit sufficient shape-retention, for example, when it is applied to a breast adjusting pad. This is particularly noticeable at a periphery of the pad, so that a final product is highly deteriorated in quality. In order to solve the problem, it would be considered to incorporate a core into the periphery of the pad to reinforce the periphery. However, this not only causes the manufacturing cost to be increased and the manufacturing to be complicated and troublesome, but leads to a danger of causing the core to be exposed by laundering. Also, it is very difficult to choose a material of sufficient hardness for the core.

SUMMARY OF THE INVENTION

The present invention has been made in view of the foregoing disadvantages of the prior art.

Accordingly, it is an object of the present invention to provide a figure adjusting pad which is capable of being suitably fitted directly to the skin.

It is another object of the present invention to provide a figure adjusting pad which is capable of exhibiting aesthetic properties and quality sufficient to be used as a part of a lingerie.

It is a further object of the present invention to provide a figure adjusting pad which is capable of exhibiting good shape-retention particularly at a periphery thereof.

It is still another object of the present invention to provide a figure adjusting pad which is capable of possessing a suitable degree of porosity.

It is yet another object of the present invention to provide a process for manufacturing a figure adjusting pad having the above-described characteristics.

In accordance with one aspect of the present invention, a figure adjusting pad which has an end portion trimmed is provided. The figure adjusting par includes a silicone gel element provided with perforations and formed into a desired shape, and a stretchable fabric for covering the silicone gel element. The perforations of the silicone gel element comprise traces formed by elution of particles incorporated in a silicone gel stock solution for the silicone gel element. The trimmed portion of the pad includes the silicone gel element and is double-sewn together with the silicone gel element.

In a preferred embodiment o#the present invention, the trimmed portion constitutes a lug positioned on a periphery of the pad.

In a preferred embodiment of the present invention, the silicone gel element has penetration of 40 to 60 measured according to JIS K2207-1980 (load: 50 g) and a void volume of 50 to 65% defined by traces of elution of the particles.

In a preferred embodiment of the present invention, the particles comprise commercially available salt.

In a preferred embodiment of the present invention, the silicone gel element is formed into a shape in conformity to the breast of a women.

In accordance with another aspect of the present invention, a process for manufacturing a figure adjusting pad is provided. The process comprises a shaping sheet adhering step of adhering a stretchable fabric and a shaping sheet to each other; a mold forming step of forming of the shaping sheet into two molds for the figure adjusting pad; a pad blank forming step of pouring a silicone gel stock solution having particles incorporated therein into a stretchable fabric side of one of the molds, intimately contacting a stretchable fabric side of the other of the molds with the silicone gel stock solution and curing the silicone gel stock solution into a desired shape in a die means while heating and pressurizing it, to thereby form a pad blank including a cured silicone gel element; a peeling step of peeling only the shaping sheet from each of the molds; a perforating step of removing the particles from the silicone gel element by elution to form the silicone gel element with perforations; a cutting-off step of cutting off an extra peripheral portion of the pad blank therefrom; and a sewing step of double-sewing a cut end of the pad blank to form the figure adjusting pad. At least one of the molds is formed with a peripheral overflow passage in the mold forming step. The silicone gel stock solution is poured in the one mold in an amount sufficient to permit the silicone gel stock solution to extend to the peripheral overflow passage and then cured in the peripheral overflow passage as well as in the one mold during the mold forming step. The pad blank is cut off at a portion thereof corresponding to the peripheral overflow passage. The pad blank is double-sewn at a cut end thereof.

Also, in accordance with the present invention, a process for manufacturing a figure adjusting pad is provided. The process comprises a shaping sheet adhering step of adhering a stretchable fabric and a shaping sheet to each other; a mold forming step of forming of the shaping sheet into two molds for the figure adjusting pad; a pad blank forming step of pouring a silicone gel stock solution having particles incorporated therein into a stretchable fabric side of one of the molds and curing the silicone gel stock solution into a desired shape in a die means while heating and pressuring it, to thereby form a pad blank including a cured silicone gel element; a mold adhering step of adhering a stretchable fabric side of the other of the molds to an exposed surface of the silicone gel element; a peeling step of peeling only the shaping sheet from each of the molds; a perforating step of removing the particles from the silicone gel element by elution to form the silicone gel element with perforations; a cutting-off step of cutting off an extra peripheral portion of the pad blank therefrom; and a sewing step of double-sewing an end of the pad blank to form the figure adjusting pad. The one mold is formed with a peripheral overflow passage in the mold forming step. The silicone gel stock solution is poured in the one mold in an amount sufficient to permit the silicone gel stock solution to extend to the peripheral overflow passage and then cured in the peripheral overflow passage as well as in the one mold during the mold forming step. The pad blank is cut off at a portion thereof corresponding to the peripheral overflow passage. The pad blank is double-sewn at a cut end thereof.

In a preferred embodiment of the present invention, the cutting-off is carried out so as to leave a portion of the pad blank corresponding to the peripheral overflow passage of the mold. Alternatively, the cutting-off step is carried out so as not to leave a portion of the pad blank corresponding to the peripheral overflow passage of the mold.

In a preferred embodiment, the particles comprise commercially available salt and the perforating step is carried out by removing the salt from the silicone gel element by elution using water to form the silicone gel element with the perforations.

BRIEF DESCRIPTION OF THE DRAWINGS

These and other objects and many of the attendant advantages of the present invention will be readily appreciated as the same becomes better understood by reference to the following detailed description when considered in connection with the accompanying drawings in which like reference numerals designate like or corresponding parts throughout, wherein:

FIGS. 3A to 3E are schematic views showing steps in a shaping sheet adhering step in a process of the present invention;

FIGS. 6A and 6B are vertical sectional views showing steps in a mold adhering step in a process of the present invention;

DETAILED DESCRIPTION OF THE PREFERRED EMBODIMENTS

Now, the present invention will be described hereinafter with reference to the accompanying drawings.

Figure 1:
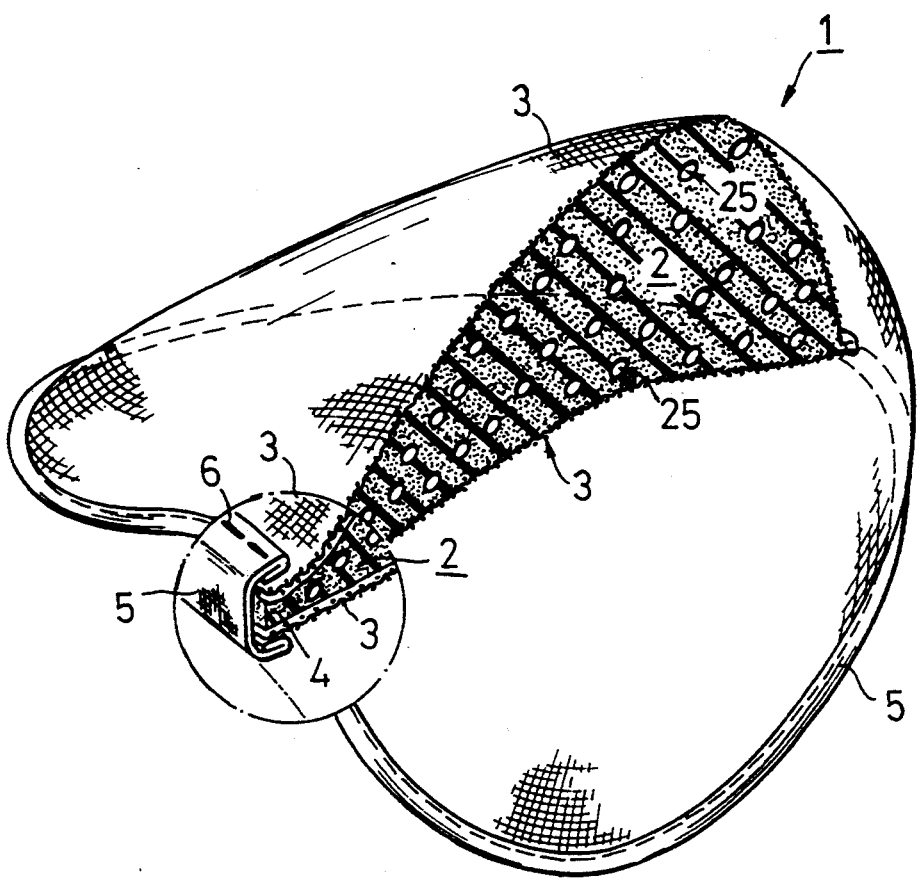
FIG. 1 is a partly cut-away perspective view showing an embodiment of a figure adjusting pad according to the present invention.

Referring first to FIG. 1 showing an embodiment of a figure adjusting pad according to the present invention, a figure adjusting pad of the illustrated embodiment which is generally designated by reference numeral 1 is in the form of a breast adjusting pad. However, the present invention is never limited to such a breast adjusting pad and is of course applicable to various parts of a human body. The figure adjusting pad 1 of the illustrated embodiment generally includes a sponge section or silicone gel element 2 having a front side expanded into a mountain-like shape and a recessed rear side and a stretchable fabric 3 applied to each of the front and rear surfaces of the sponge section 2 or silicone gel element.

The sponge section 2 comprises a porous silicone gel element, and thus exhibits suitable elasticity. Silicone gel suitable for use for the sponge section or silicone gel element 2 is an addition reaction type silicone polymer obtained by curing a mixture of diorganopolysiloxane (hereinafter referred to as "ingredient A") expressed by the following formula (1):

$$RR^1{}_2SiO-(R^2{}_2SiO)_nSiR^1{}_2R \qquad (1)$$

wherein R is an alkenyl group, $R^1$ is a monovalent hydrocarbon radical free of any aliphatic unsaturated bond, $R^2$ is a monovalent aliphatic hydrocarbon radical (a methyl group content in $R^2$ being at least 50 mol %, and an alkenyl group content in $R^2$ being 10 mol % or less when it contains an alkenyl group), n is a value sufficient to permit the ingredient A to have viscosity of 100 to 100,000 cSt at a temperature of 25° C., and organohydrogenpolysiloxane (hereinafter referred to as "ingredient B") which has viscosity of 5000 cSt or less at a temperature of 20° C. and hydrogen atoms bonded directly to at least two Si atoms in one molecule thereof, which mixture is so adjusted that a ratio (molar ratio) of the sum total of alkenyl groups contained in the ingredient A to the sum total of hydrogen atoms bonded directly to Si atoms in the ingredient B is 0.1 to 2.0.

Now, the silicone gel will be described in more detail. The gradient A is a compound having a straight-chain molecular structure wherein alkenyl groups R at both ends of the molecule add to hydrogen atoms bonded directly to Si atoms in the ingredient B to form a cross-linking structure. The alkenyl groups present at both terminals of the molecule are each preferably a lower alkenyl group. The alkenyl group is particularly preferably a vinyl group in view of reactivity.

Also, $R^1$ present at each of the terminals of the molecule is a monovalent hydrocarbon radical free of any aliphatic unsaturated bond and includes, for example, an alkyl group such as a methyl group, a propyl group, a hexyl group or the like; a phenyl group; and a fluoroalkyl group.

In the formula (1) described above, $R^2$ is a monovalent aliphatic hydrocarbon radical and includes, for example, an alkyl group such as a methyl group, a propyl group, a hexyl group or the like and a lower alkenyl group such as a vinyl group or the like. Also, $R^2$ contains at least 50 mol % of methyl group. When $R^2$ contains an alkenyl group, the content is preferably 10 mol % or less. The presence of alkenyl more than 10 mol % in $R^2$ causes crosslinking density of the ingredient to be excessively high, resulting in the viscosity being excessively increased. n is set to be a value sufficient to permit the ingredient A to possess viscosity of 100 to 100,000 cSt at a temperature of 25° C. and preferably within the range of from 200 to 20,000 cSt.

The ingredient B is a crosslinking agent for the ingredient A, wherein the hydrogen atoms bonded directly to the Si atoms add to alkenyl groups in the ingredient A to cure the ingredient A. Various kinds of materials having molecular structures such as a straight-chain structure, a branched-chain structure, a cyclic structure, a net structure and the like may be used for the ingredient B, so long as they exhibit the above-described function of the ingredient B.

To the Si atoms in the ingredient B are bonded organic groups in addition to the hydrogen atoms. The organic groups each are normally a lower alkyl group such as a methyl group. Viscosity of the ingredient B at 25° C. is set to be normally 5000 cSt or less and preferably 500 cSt or less. The ingredient B of such a structure includes organohydrogenpolysiloxane of which both terminals each are blocked with a triorganosiloxane group. a copolymer of diorganosiloxane and organohydrogensiloxane, tetraorgano-tetrahydrogensiloxane, a copolymer siloxane of ½ unit of $HR^1{}_2SiO$ and 4/2 units of SiO, and a copolymer polysiloxane of ½ unit of $HR^1{}_2SiO$, ½ unit of $R^1{}_2SiO$ and 4/2 units of SiO. $R^1$ is the same as described above with respect to the formula (1).

Subsequently, the ingredients A and B are mixed so that a ratio of the total molar amount of alkenyl groups in the ingredient A to the total molar amount of hydrogen atoms bonded directly to the Si atoms in the ingredient B is normally between 0.1 and 2.0 and preferably between 0.1 and 1.0, and then subject to a curing reaction.

The curing reaction normally takes place using a catalyst. The catalyst suitable for use for this purpose is a platinum catalyst. The platinum catalyst includes, for example, finely ground elemental platinum, chloroplatinic acid, platinum oxide, a complex salt of platinum and olefin, and a complex of platinum alcoholate, chloroplatinic acid and vinylsiloxane. Such complex salts are each used in an mount of 0.1 ppm or more (in platinum equivalent) and preferably 0.5 ppm or more based on the sum total weight of the ingredients A and B. The upper limit of the amount of the catalyst used is not specified; however, when it can be used in the form of liquid or solution, the sufficient amount is 200 ppm or less.

The ingredients A and B are mixed with the catalyst and the resultant mixture is then left to stand at a room temperature or heated, resulting in curing thereof, so that the silicone gel described above is prepared. Measurement according to JIS (Japanese Industrial Standard) K-2207-1980 (load: 50 g) indicates that the silicone gel thus obtained normally exhibits penetration of 5 to 250. Hardness of the silicone gel is varied depending on the crosslinking structure formed between the ingredient A and the ingredient B.

Viscosity of the silicone gel before curing and its penetration after curing may be adjusted by previously adding silicone oil having methyl groups at both terminals thereof to the silicone gel obtained in an amount of 5 to 75% by weight. The silicone gel is thus adjusted.

Alternatively, a commercially available silicone gel may be used to this end.

The commercially available silicone gel includes, for example, DF5027, TOUGH-3, TOUGH-4, TOUGH-5, TOUGH-6 and TOUGH-7 each manufactured by Toray Dow Corning Silicone Kabushiki Kaisha; X32-902/CAT1300 manufactured by Shin-Etsu Kagaku Kabushiki Kaisha; F250-121 manufactured by Nippon Yunika Kabushiki Kaisha; and the like.

Silicone gel for the sponge section 2 may include, in addition to the above described ingredients A and B and catalyst, an agent providing thixotropic properties, a pigment, a cure retarder, a flame retarder and a filler, as well as a finely powdered deodorizer mainly consisting of oxide, water-absorbent resin and the like so long as they do not deteriorate characteristics of the silicone gel. Also, microballoons may be incorporated as a filler in silicone gel. For this purpose, fillers sold under "Fillite" (registered trademark) and "EXPANCEL" from Nippon Fillite Kabushiki Kaisha are commercially available.

The silicone gel thus formulated is cured, resulting in the provision of the sponge section or silicone gel element.

The stretchable fabric 3 may be formed of, a longitudinally and laterally stretchable fabric material such as, for example, a fabric material for forming stockings, a fabric material like a knitted fabric, a tricot fabric material, a tubular knitted fabric material or the like. For such a fabric material for the stretchable fabric 3, polyester fibers, polyurethane fibers or the like may be used. The fabric material may be subject to napping or raising. The stretchable fabric 3 has a rear surface defined on a side thereof contacted with the silicone gel element 2 and a front surface defined on the opposite thereto.

Figure 10:
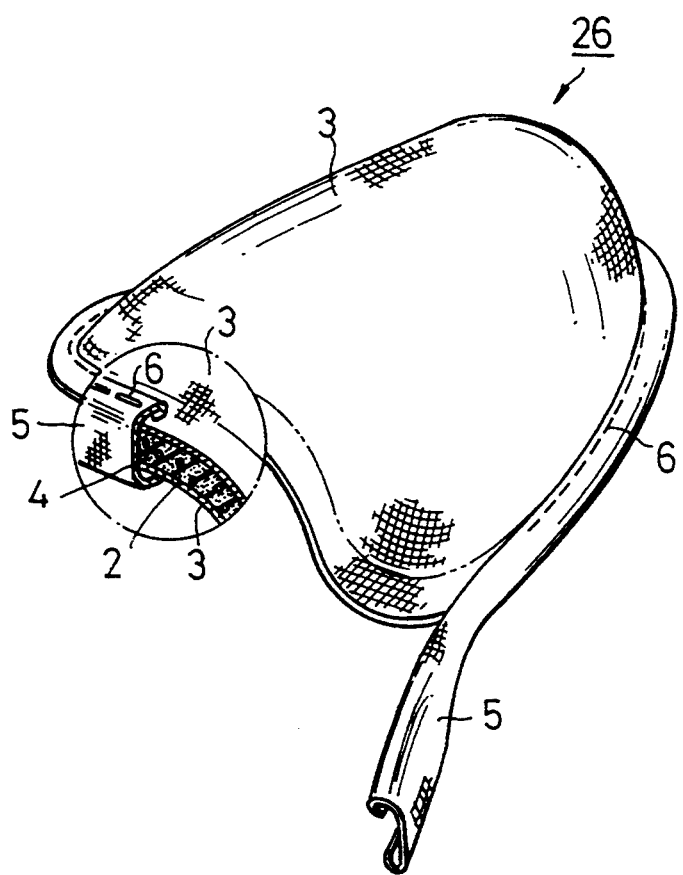
FIG. 10 is a perspective view showing a sewing step in a process of the present invention.

The sponge section or silicone gel element 2 is formed at a periphery thereof with a lug 4. The lug 4, as shown in FIG. 10, is adapted to be double-sewn together with the silicone gel element 2 by a thread 6 while a thin layer of the porous silicone gel element 2 is kept interposed between the upper stretchable fabric 3 and the lower stretchable fabric 3 and kept covered at an end thereof with a trimming fabric 5. The lug 4 constitutes an expansion of a substantially uniform thickness as small as several millimeters which projects outwardly from the periphery of the sponge section or silicone gel element 2 having a desired contour. Such construction is one of features of the present invention and permits the silicone gel of the lug 4 to be compressed. This results in the lug 4 being hardened as if a core is incorporated in the lug 4, so that a periphery of the pad 1 may exhibit satisfactory shape-retention.

Now, a process for manufacturing such a breast adjusting pad 1 will be described hereinafter.

First, solvent-soluble particles are incorporated into a silicone gel stock solution, which is then subject to a curing treatment, resulting in a cured silicone gel material. Then, the particles are eluted from the material in a solvent to form voids in the material, to thereby provide a porous silicone gel element. When the solvent is water, the soluble particles may be formed of sodium polyacrylate, polyvinyl alcohol, methyl cellulose, carboxy methyl cellulose, ethylene oxide, polyvinyl pyrrolidone, acrylic amide, glue, gelatin, casein, polypeptide, funori (glue plant), agar, sodium alginate, sodium chloride, dextrose and glucose, saccharose, natural polysaccharide such as prulan, xanthane gum or starch, sodium ascorbate, or the like. When acetone, ethanol, methanol or the like can be used as the solvent in view of a material for a mold or the like, the particles may be made of polyvinyl alcohol, methyl cellulose, ethyl cellulose, water-soluble nylon, shellac, styrol or the like.

Mere preparation of a porous silicone gel may be carried out according to an extinguishing method wherein a material extinguished by heating is incorporated into a silicone gel stock solution to prepare a mixture, which is then cured by heating, and then the material is extinguished by heating; a shrinking method by drying wherein a swelled material incorporated in a silicone gel stock solution is shrunk by drying and then separated; a microwave heating method wherein volatile liquid of a large dielectric loss coefficient is dispersed in a silicone gel stock solution and then subject to dielectric heating in an electric field of a high frequency, such that it is increased in temperature so as to be expanded by vaporization and the silicone gel stock solution is cured by crosslinking; or the like.

However, the figure adjusting pad of the present invention is required to exhibit satisfactory touch (or feel), air-permeability and quality. Unfortunately, the above-described methods each fail to provide the figure adjusting pad of the present invention with such properties. More particularly, application of the stretchable fabrics to the silicone gel element with increased adhesion after the silicone gel element is formed with perforations fails to provide the pad with satisfactory touch, air-permeability and quality. Thus, the present invention employs an elution method wherein the silicone gel stock solution is cured in a manner to be entangled in the the stretchable fabric to produce the silicone gel element and then the silicone gel element is subject to a perforating treatment.

Now, an embodiment of a process of the present invention wherein water is used for the solvent and sodium chloride is used for the particles will be described with reference to Figs. 2 to 9. The process generally comprises a feedstock mixing step, a shaping sheet adhering step, a mold forming step, a pad blank forming step, a mold adhering step, a cutting-off step, a perforating step and a sewing step.

1. Feedstock Mixing Step

Figure 2:
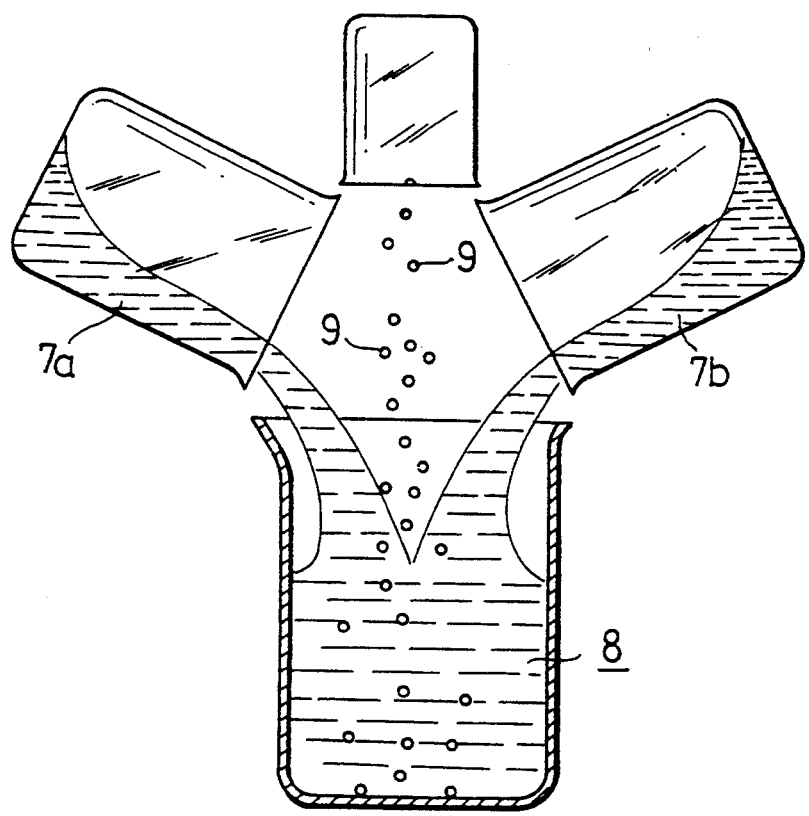
FIG. 2 is a schematic view showing a feedstock mixing step in a process for manufacturing a figure adjusting pad according to the present invention.

As shown in FIG. 2, an A agent 7a of silicone gel and a B agent 7b thereof, a catalyst, sodium chloride 9 for particles eluted after curing, and any optional ingredients such as a pigment and the like are mixed together to prepare a silicone gel stock solution 8. Commercially available salt may be used as the sodium chloride for the particles. This is due to the fact that the salt is uniform in particle size and permits disposal of a waste solution produced after elution of the salt to be facilitated. Also, the salt is relatively inexpensive and permits the elution to be relatively readily carried out.

In the illustrated embodiment, the silicone gel stock solution 8 is formed by incorporating 300 parts of the salt into 100 parts of a combination of the A agent 7a, B agent 7b and catalyst prepared so as to have penetration of 50 measured according to JIS K2207-1980 (load: 50 g). This results in providing a silicon gel element perforated into a void volume as high as about 60% after the perforating step described hereinafter. The silicone gel element thus obtained, when pushed with a finger, exhibits touch, elasticity and restoration which substantially approach the characteristics of the breast of a woman, such that it is particularly suitable for use as a breast adjusting pad. Silicone gel which has penetration of 40 to 60 and a void volume of 50 to 65% is likewise suitably applicable to the breast adjusting pad. When the salt is used for the figure adjusting pad including the breast adjusting pad and the like, it is convenient that the silicone gel stock solution is prepared by incorporating 150 to 450 parts of the salt into 100 parts of the combination of the A agent, silicone gel B agent and catalyst.

2. Shaping Sheet Adhering Step

This step is for adhering a stretchable fabric and a shaping sheet to each other by means of a water-soluble adhesive interposed therebetween. In this step, first of all, a shaping sheet 11 which comprises a rigid vinyl chloride sheet of 0.2 to 1.0 mm in thickness, a stretchable fabric 3 of a somewhat large thickness such as a knitted tricot fabric, and a polyvinyl alcohol film 12 acting as a water-soluble adhesive agent each are cut into a size of 280 mm×280 mm, as shown in FIG. 3A.

Then, as shown in FIG. 3B, the stretchable fabric 3 is immersed into water and then lightly squeezed by hands to a degree sufficient to prevent droplets from dropping from the fabric 3. Subsequently, as shown in FIG. 3C, the vinyl chloride sheet 11, polyvinyl alcohol film 12 and stretchable fabric 3 are upward 14 superposed on each other in turn and then interposed between two aluminum plates 13. Then, they are subject to a pressing treatment using a vulcanizing pressing machine 14. This causes water kept in the stretchable fabric 3 to exude therefrom, so that the polyvinyl alcohol film 12 may be dissolved in the water to lead to gelatinization, resulting in the stretchable fabric 3 and vinyl chloride sheet 11 being adhered together. It is preferable that the amount of water kept in the stretchable fabric 3 is suitably adjusted to prevent the water from exuding to the rear surface of the stretchable fabric 3. This is for the reason that the presence of polyvinyl alcohol on the rear surface of the stretchable fabric 3 which is a surface to be contacted with the silicone gel element causes adhesion between the silicone gel and the stretchable fabric 3 to be reduced.

In this connection, a coating of hydrogensiloxane corresponding to the B component of the silicone gel stock solution on the rear surface of the stretchable fabric 3 promotes crosslinking on the coated surface, to thereby reduce stickiness, and thereby reinforce the adhesion. Also, a coating of primer strengthens adhesion to the fabric.

Then, as shown in FIG. 3E, a combination of the stretchable fabric 3, polyvinyl alcohol 12 and vinyl chloride sheet 11 thus adhered together through the polyvinyl alcohol sheet 12 is taken out from the vulcanizing pressing machine 14 the aluminum plates 13 are removed from the combination, and the combination is then dried at 60° to 70° C. for thirty minutes. In the illustrated embodiment, gelatinization of the polyvinyl alcohol film 12 is carried out by suitably wetting the stretchable fabric 3. Alternatively, polyvinyl alcohol in the form of liquid or any other water-soluble adhesive may be applied to the polyvinyl chloride sheet 11. In this instance, the polyvinyl alcohol film 12 is not necessarily required.

In the illustrated embodiment, a vinyl chloride sheet is used as the shaping sheet 11. Alternatively, any other suitable thermoplastic sheet or a polyvinyl alcohol sheet made into a thickness larger than the polyvinyl alcohol film 12 may be used for this purpose. In this instance, the polyvinyl alcohol sheet acts as both a shaping sheet and a water-soluble adhesive.

In the illustrated embodiment, the shaping-sheet adhering step is initially carried out in the manufacturing process of the present invention. Alternatively, polyvinyl alcohol is applied to the front surface of the stretchable fabric 3 in an amount suitable for preventing it from exuding to the rear surface of the fabric 3 and then dried to carry out mass-production of the stretchable fabric 3 having laminate-like polyvinyl alcohol attached thereto. This permits the manufacturing process to be initiated at the next mold forming step. Adhesion of the shaping sheet to the stretchable fabric while applying the water-soluble adhesive such as polyvinyl alcohol or the like in a relatively large amount all over the shaping sheet permits the adhesive to suitably penetrate into the stretchable fabric 3 while preventing it from exuding to the rear surface of the fabric 3, resulting in the subsequent peeling step and perforating step being substantially concurrently carried out in water and the necessity applying of excessive force to the pad during the peeling step being eliminated. Also, this permits the front surface of the stretchable fabric to be finished so as to exhibit relatively dry touch after the perforating step, so that the resultant figure adjusting pad may provide a user with excellent touch. Water-soluble adhesive such as polyvinyl alcohol or the like may be insufficient to adhere the stretchable fabric to the vinyl chloride sheet. In such a case, a synthetic adhesive may be used for reinforcing the adhesion.

Alternatively, a water-soluble adhesive or a non-aqueous adhesive such as a synthetic rubber adhesive or the like may be sprayed in the form of a thin film to adhere the vinyl chloride sheet 11 to the stretchable fabric 3 while ensuring sufficient adhesion strength sufficient to permit the shaping sheet 11 to endure the mold forming step. In this instance, when the peeling step is carried out under the conditions that the mold is kept hot immediately after the mold forming step, the mold is readily peeled with the assistance of the softened shaping sheet 11 without applying excessive force thereto and dissolving the adhesive.

Also, this permits the silicone gel element to penetrate to a position near the front surface of the stretchable fabric 3, so that the resultant pad may exhibit touch (feel) similar to the skin. This may be accomplished by spraying a commercially available spray adhesive on the shaping sheet 11 to form a thin film of the adhesive, superposing the stretchable fabric 3 on the adhesive, and then adhering the fabric 3 to the shaping sheet 11 through the adhesive while smoothing out wrinkles from the fabric by means of an iron or the like.

Further, the A or B agent free of the salt or the silicone gel stock solution in which the A and B agents are mixed is applied to the rear surface of the stretchable fabric before the silicone gel stock solution containing the salt is poured into one of the molds, to thereby wipe off any extra matter therefrom. Such a treatment likewise may be made on the other mold. Such a treatment aids in reinforcing the adhesion, and improves finishing of the surface and extension of the silicone gel stock solution during filling of the solution.

3. Mold Forming Step

The step is to form the shaping sheet 11 to which the stretchable fabric 3 is adhered into a mold for the breast adjusting pad. In the process of the present invention, two molds are used which comprise one mold for forming a mountain-like shape on the front side of the breast adjusting pad and the other mold for forming a recessed shape on the rear side of the pad. The mold formed in the present step is the former or one mold. When one mold and the other mold are required to be distinguished from each other, the former will be referred to as "mountain forming mold" designated at reference numeral 16 and the latter will be referred to as "recess forming mold" designated at 17.

Figure 4A:
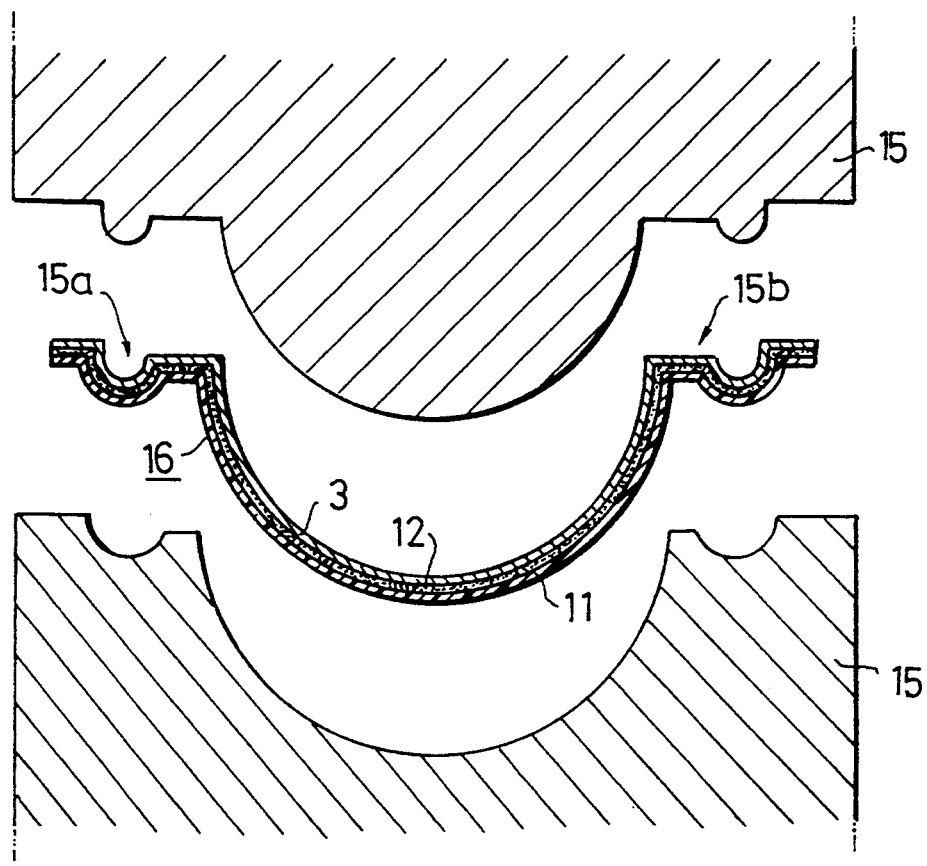
FIG. 4A is a vertical sectional view showing a mold forming step in a process of the present invention.
Figure 4B:
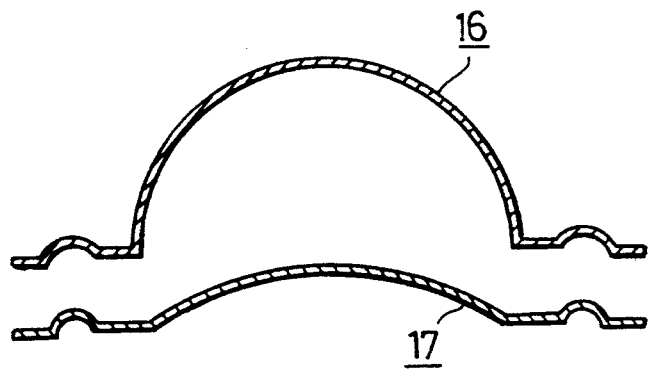
FIG. 4B is a vertical sectional view showing molds formed by the mold forming step shown in FIG. 4A.

In the step, as shown in FIGS. 4A and 4B, the vinyl chloride sheet 110 polyvinyl alcohol film 12 and stretchable fabric 3 which have been integrated as described above are formed into the mold 16 of a breast-like shape by means of a vacuum mold forming machine 15. The mountain forming mold 16 is formed on a whole periphery thereof with an overflow receiving groove 15a for receiving an overflow of the silicone gel stock solution poured into the mold and a peripheral overflow passage 15b for guiding the overflow from the mold 16 to the overflow receiving groove 15a. A mold forming machine utilizing a compressed air pressure may be substituted for the vacuum forming machine 15. Alternatively, a combination of both may be suitably used. In the present step, the recess forming mold 17 of a similar structure is also formed. The peripheral overflow passage 15b may be formed on any one of the molds 16 and 17.

4. Pad Blank Forming Step

Figure 5A:
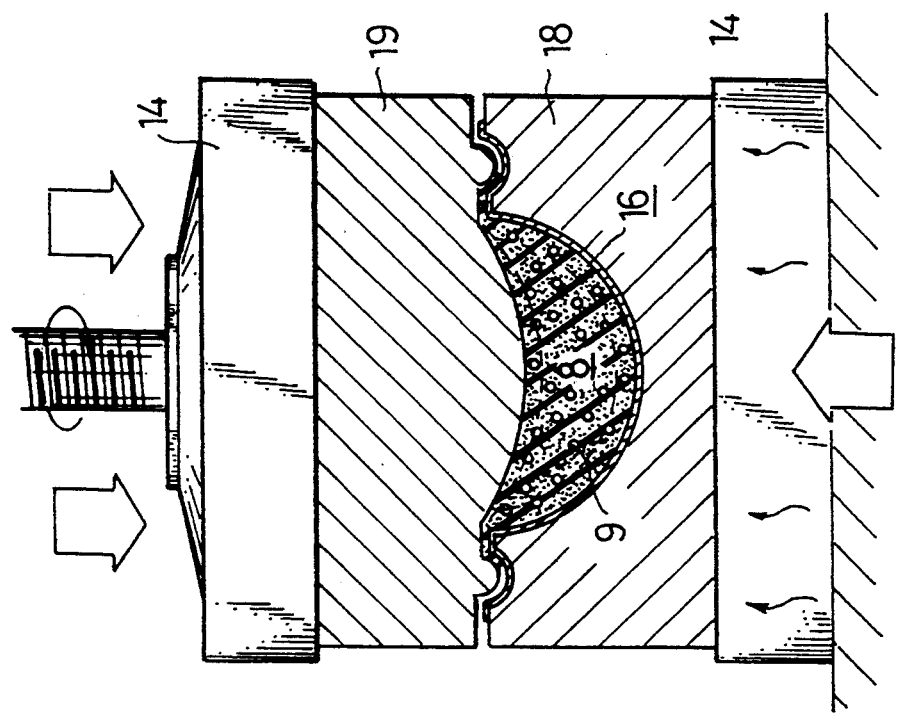
FIGS. 5A and 5B are vertical sectional views showing steps in a pad blank forming step in a process of the present invention.

The step is to pour the silicone gel stock solution 8 into which salt 9 is incorporated in the vinyl chloride sheet 11 formed into the mold in the previous mold forming step and then cure it by heating. More particularly, as shown in FIG. 5A, a predetermined amount of silicone gel stock solution 8 is carefully charged in the mountain forming mold 16 so as to conform to the shape of the mold 16. The amount of silicone gel stock solution to be charged is determined depending on the size of the mountain forming mold 16. In general, the amount of silicone gel stock solution is so determined that when a male die is put on the mountain forming mold 16, it forces out a part of the silicone gel stock solution 8 from the mountain forming mold 16 to cause it to flow out to substantially the whole region of the peripheral overflow passage 15b or at least the whole periphery of the passage 15b and to partially extend to the overflow receiving groove 15a.

Charging of the silicone gel stock solution 8 in the mountain forming mold 16 is preferably carried out in such a manner that the silicone gel stock solution 8 of a somewhat low salt content (for example, gel:salt=1:3.0) is applied to a portion of the stretchable fabric 3 in proximity to a surface thereof contacted with the vinyl chloride sheet 11 and the silicone gel stock solution 8 of a somewhat high salt content (for example, gel:salt=1:3.3) is charged in a central portion of the mold. This facilitates dissolving of the salt in the perforating step. Also, such dissolving of salt in the perforating step is further promoted by applying the silicone gel stock solution to which the salt of a large grain size or urea of a fine particle size is added to the portion of stretchable fabric 3 in proximity to its surface contacted with the vinyl chloride sheet 11.

Figure 5B:
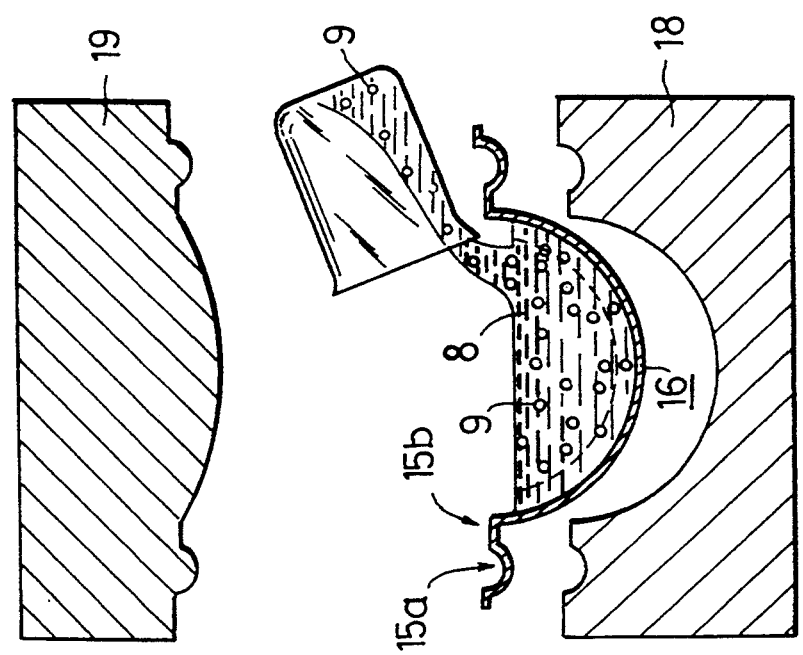

Then, as shown in FIG. 5B, the mountain forming mold 16 thus charged with the silicone gel stock solution 8 is placed in a female die 18 formed in conformity with the mold 16 and then is covered with a male die 19. This causes an excessive part of the silicone gel stock solution 8 to flow out to the peripheral overflow passage 15b. The salt is generally inferior in flowability to the silicone gel stock solution. Therefore, in the silicone gel stock solution 8 charged, silicone gel flows while separating from the salt to cause traces of salt to be formed in the silicone gel, resulting in the final products being adversely affected. Application of vibration to the dies and therefore the silicone gel stock solution 8 prior to application of pressure thereto permits the silicone gel stock solution to uniformly and slowly flow, to thereby effectively eliminate such a disadvantage. Thereafter, a vibration means may be set on the dies to vibrate them. Then, the dies 18 and 19 are placed in the vulcanizing pressing machine 14, wherein a pressure is applied to the dies and is gradually increased, to thereby cause the silicone gel stock solution 8 to flow in conformity with the recess forming mold 17, and then it is heated for curing.

When the silicone gel stock solution 8 is cured to a certain degree, the mountain forming mold 16 having the silicone gel received therein is taken out from the dies 18 and 19 and then placed in a heating oven 21 to fully cure the silicone gel stock solution. The above-described curing procedure in the illustrated embodiment, wherein the mountain forming mold 16 is charged with the silicone gel stock solution and then the recess forming mold 17 is put on the mountain forming mold 16 is effective to contribute to simplification of manufacture and reduction in manufacturing cost.

5. Mold Adhering Step

The silicone gel element cured in the mountain forming mold 16 has a recess 22 formed by the male die 19. This step is for adhering the recess forming mold 17 to the thus-formed recess 22. More specifically, first of all, any release agent or oil adhering to the recess 22 of the silicone gel cured in the mountain forming mold 16 is fully wiped off therefrom by means of a suitable solvent. Then, as shown in FIGS. 6A and 6B, a suitable amount of adhesive 23 is uniformly applied to the so-degreased recess 22. Excessive application of the adhesive 23 causes the stretchable fabric 3 provided on the recess 22 to be stained. Also, in order produce suitable adhering force, the application is preferably carried out after the silicone gel element is cooled to room temperature. Then, the recess forming mold 17 is put on the adhesive 23 and then gradually pressurized by means of the vulcanizing pressing machine 14, resulting in it being pressed into contact with the recess 22. Then, it is heated to cure the adhesive.

In the illustrated embodiment, the pad blank forming step, as described above, is carried out in a manner to contact the male die 19 directly with the cured silicone gel stock solution without using the recess forming mold 17 to cure it and then adhere the recess forming mold 17 to the recess 22. Alternatively, the pad blank forming step may employ a procedure of, prior to covering of the silicone gel stock solution 8 with the male die 19, placing the recess forming mold 17 under the male die 19 to intimately contact it with the silicone gel stock solution and then curing the silicone gel stock solution to adhere both to each other, to thereby eliminate the above-described step of adhering the recess forming mold 17. Such a procedure leads to rationalization of the manufacturing.

However, the mold adhering step of adhering the recess forming mold 17 employed in the illustrated embodiment exhibits various advantages. More specifically, the silicone gel stock solution 8 is relatively inferior in flowability. Also, when the stretchable fabric 3 is formed at the periphery thereof with the lug 4 which is then subject to double-sewing, it is required to narrowly form the peripheral overflow passage 15b in order to form the lug as thinly as possible in view of aesthetic feeling of the final product. Unfortunately, this causes a so-called cavity to be formed in the final product or causes a failure in uniform distribution of the perforations throughout the final product. Also, this fails to satisfactorily remove air entering between the silicone gel stock solution and the recess forming mold 17, leading to a failure in adhesion of the recess forming mold 17. The mold adhering step is effective to solve such problems and increases the yield.

6. Peeling Step

Figure 7:
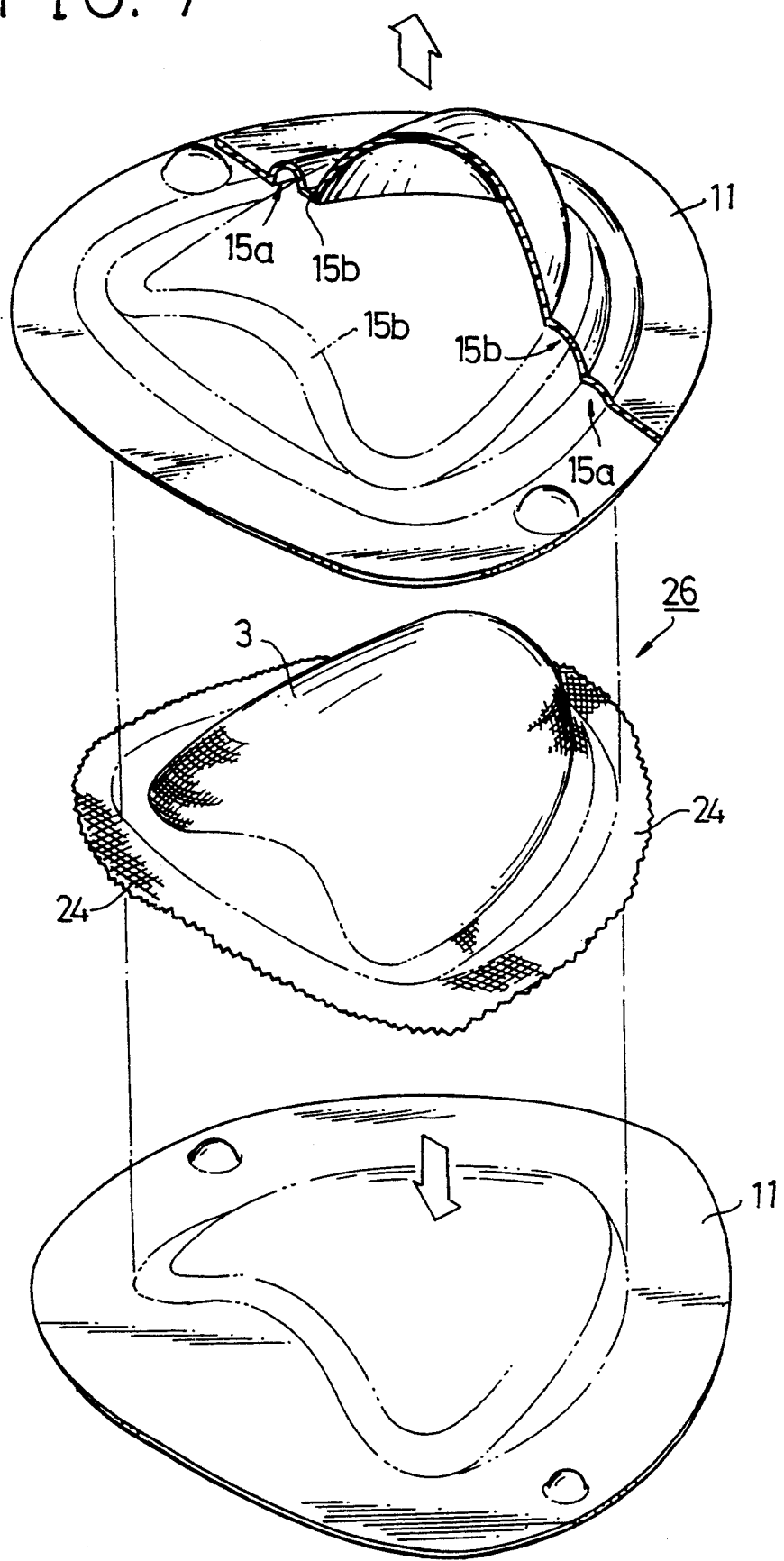
FIG. 7 is an exploded perspective view showing a peeling step in a process of the present invention.
Figure 8:
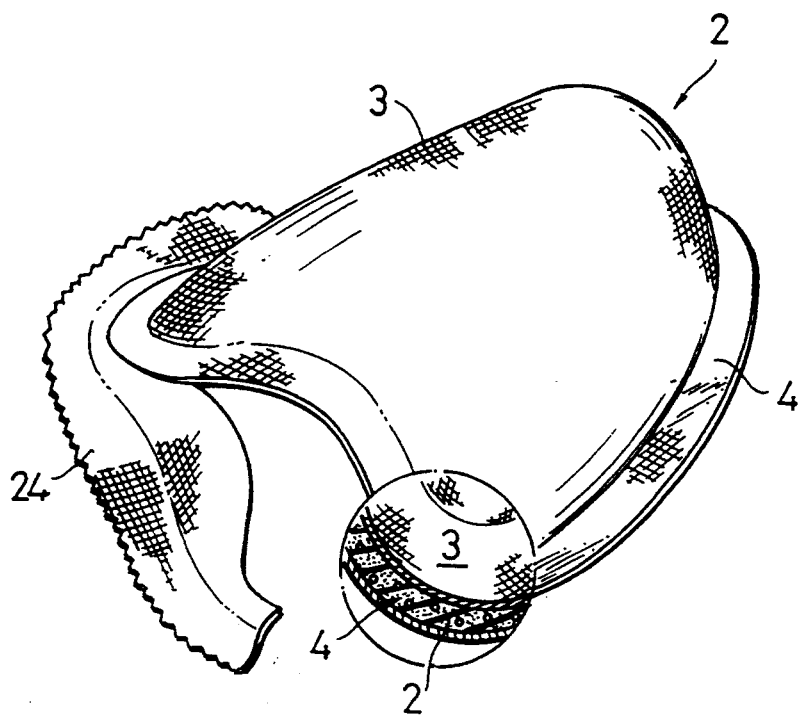
FIG. 8 is a perspective view showing a cutting-off step in a process of the present invention.

After curing the adhesive, the vinyl chloride sheet 11 is peeled from the stretchable fabric 3 while being kept softened by heat, as shown in FIG. 7. At this time, the stretchable fabric 3 is kept adhered to the cured silicone gel element. Therefore, peeling of the vinyl chloride sheet 11 should be carefully carried out while preventing separation of the stretchable fabric 3 from the silicone gel element. Further, when the shaping sheet 11 and stretchable fabric 3 are relatively firmly adhered to each other by means of the water-soluble adhesive as described above, peeling of the shaping sheet 11 from the stretchable fabric 3 may be carried out by dissolving the water-soluble adhesive during the subsequent perforating step in which immersion in water takes place.

7. Cutting Step

Figure 9:
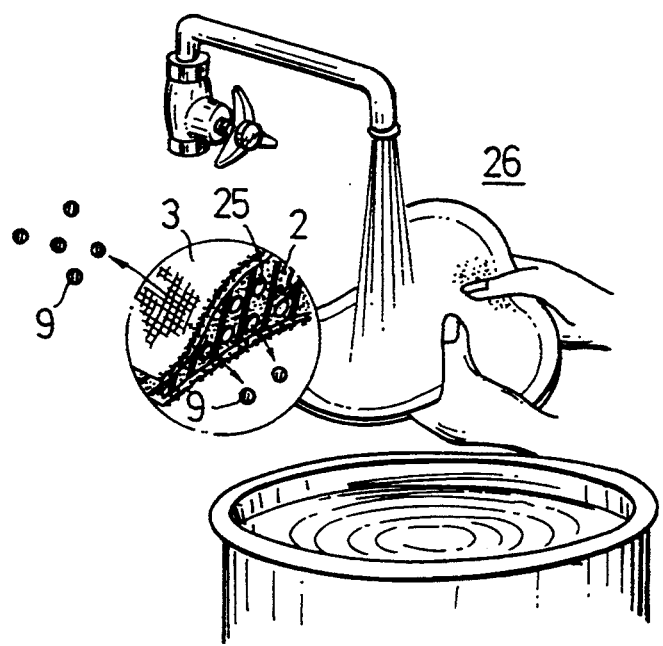
FIG. 9 is a perspective view showing a perforating step in a process of the present invention.

The silicone gel element as peeled from the vinyl chloride sheets 11 has an extra peripheral portion 24 formed by the peripheral overflow passage 15b and overflow receiving groove 15a of the mold 16. Therefore, the extra portion 24 is cut off to cause the silicone gel element to be exposed at a periphery thereof to prepare a pad element 26 (FIG. 9). This facilitates elution of the salt 9 from the exposed silicone gel during the subsequent perforating step.

Also, in this step, the extra peripheral portion 24 may be cut off so as to substantially determine a contour or configuration of the breast adjusting pad. Alternatively, the cutting-off may be carried out only for the purpose of exposing the peripheral end of the silicone gel element described above. In the latter case, the cutting-off operation is carried out for providing the periphery with a shape required for the final product 1. Cutting-off of the portion 24 at a distal end of the peripheral overflow passage 15b or lug 4 facilitates the cutting-off operation. Also, it leaves the lug 4 which is then subject to double-sewing, to thereby facilitate the double-sewing operation to provide the final product with an aesthetic feeling. In the illustrated embodiment, the cutting-off may be carried out so as to leave the peripheral passage 15b or lug 4 of 3 mm. This leads to satisfactory finishing of the final product 1.

On the contrary, performing the cutting-off step in a manner not to leave the lug 4 causes the double-sewing step to be troublesome because it causes a cut surface of the fabric 3 to be oblique. Also, this renders a line of the double-sewing non-uniform, and thereby tends to fail to provide the final product with aesthetic feeling. Further, this causes trimming to be rather conspicuous to a degree sufficient to deteriorate quality of the final product. Thus, it is generally convenient that the cutting-off is carried out while leaving the peripheral overflow passage 15b.

8. Perforating Step

This step is for removing the salt 9 in the cured silicone gel element due to elution of the salt by water, to thereby form voids or perforations 25 in the silicone gel element. In order to facilitate elution of the salt 9 from the silicone gel element, it is first carried out to take off the stiffness of the cured silicone gel element to cause adjacent spaces in the silicone gel element occupied by the salt 9 to be contiguous to each other. Then, the pad element 26 is immersed in water to dissolve the salt 9. This is carried out by washing it using a laundry machine or washing it by hand while crumpling it to substantially elute the salt 9 from the silicone gel element. Also, desalting for finishing takes place by exposing the pad element to a water jet to fully remove the salt. Then, the pad element is dried in an air dryer. The resultant pad element possesses flexibility, elasticity and massive feeling similar to a human body. In particular, it exhibits excellent touch as compared with the prior art.

9. Sewing step

The pad element 26 thus obtained is subject at an end thereof such as the lug 4 and the like to a sewing treatment. More particularly, as shown in FIG. 10, a trimming fabric 5 is applied to the lug 4 of the pad element 26 so as to surround it. Then, a whole periphery of the lug 4 is double-sewed through the trimming fabric 5 by means of the thread 6. This causes the porous silicone gel element to be compressed, so that it is hardened to act as a core of the lug. Thus, the lug 4 is shaped, resulting in the final product or breast adjusting pad 1 being obtained.

More particularly, the above-described trimming permits the core to be formed in the lug to effectively establish the whole configuration of the breast adjusting pad, resulting in the pad exhibiting satisfactory shape retention. Also, a portion of the porous silicone gel element positioned outside the thread 6 is permitted to expand due to its restoring force, to thereby cause the trimming fabric 5 to expand. Thus, the breast adjusting pad exhibits high quality. The portion of the porous silicone gel element outside the thread 6 may be formed into a width of about 1 to 2 mm. Therefore, it will be noted that the breast adjusting pad 1 of the illustrated embodiment is favorably accepted as a part of a lingerie and contributes to figure adjusting. After the sewing, the breast adjusting pad 1 may be coated with a body powder to remove surface tackiness from the pad 1. The body powder may mainly consist of mica.

The illustrated embodiment has been described in connection with the breast adjusting pad. However, the figure adjusting pad of the present invention is not limited to such a breast adjusting pad. For example, it may be effectively applicable to a pad for a brassiere for plumping the breasts, a shoulder pad, a knee pad, a waist pad and the like.

As can be seen from the foregoing, the figure adjusting pad of the present invention is so constructed that the lug is subject to double-sewing together with the porous silicone gel. Such construction permits the lug to be hardened to a degree sufficient to serve as a core for shape retention due to the sewing, resulting in the figure adjusting pad exhibiting satisfactory shape retention and restoration.

Also, in the process of the present invention, the silicone gel stock solution is poured in the mountain forming mold so as to spread over the whole peripheral overflow passage. Thus, when the lug is formed so as to leave the silicone gel received in the passage, double-sewing of the lug is facilitated and the figure adjusting pad is provided with aesthetic properties. Further, independent practicing of the mold adhering step ensures firm adhesion between the silicone gel element and the recess forming mold, to thereby significantly increase the yield.

While preferred embodiments of the invention have been described with a certain degree of particularity with reference to the drawings, obvious modifications and variations are possible in light of the above teachings. It is therefore to be understood that within the scope of the appended claims, the invention may be practiced other than as specifically described.

What is claimed is:

1. A figure adjusting pad comprising
   a silicone gel element having a predetermined shape including an inner portion and an outer peripheral portion about a periphery of said inner portion;
   a stretchable fabric covering said silicone gel element in such a manner that an outermost edge of said outer peripheral portion of said silicone gel element is exposed outwardly from said stretchable fabric;
   wherein said silicone gel element has perforations formed therein which comprise traces formed by elution of particles incorporated in a silicone gel stock solution for said silicone gel element;
   wherein said inner portion of said silicone gel element varies in thickness depending on location;
   wherein said stretchable fabric and said outer peripheral portion of said silicone gel element are double-sewn at a predetermined location inwardly of said outermost edge of said outer peripheral portion in such a manner as to compress a portion of said outer peripheral portion of said silicone gel element and form an expanded portion outwardly of said predetermined location, said expanded portion having a thickness less than that of said inner portion of said silicone gel element; and
   wherein said silicone gel element has a penetration of 40 to 60 measured according to JIS K2207-1980 (load: 50 g) and a void volume of 50 to 65% defined by said traces of elution of said particles.

2. A figure adjusting pad as defined in claim 1, wherein said particles comprise salt.

3. A figure adjusting pad as defined in claim 1, wherein said silicone gel element is formed into a shape in conformity to a breast of a woman.

4. A figure adjusting pad as defined in claim 1, wherein said particles comprise salt.

5. A figure adjusting pad as defined in claim 1, wherein said silicone gel element is formed into a shape in conformity to a breast of a woman.

6. A process for manufacturing a figure adjusting pad, comprising:
   a shaping sheet adhering step for adhering a stretchable fabric and a shaping sheet to each other;
   a mold forming step for forming said shaping sheet into two molds;
   a pad blank forming step for pouring a silicone gel stock solution having particles incorporated therein into a stretchable fabric side of one of said molds, intimately contacting a stretchable fabric side of the other of said molds with said silicone gel stock solution and curing said silicone gel stock solution into a desired shape in a die while heating and pressurizing it, to thereby form a pad blank including a cured silicone gel element;

a peeling step for peeling only said shaping sheet from each of said molds;

a perforating step for removing said particles from said silicone gel element by elution to provide said silicone gel element with perforations;

a cutting-off step for cutting off an extra peripheral portion of said pad blank therefrom; and a sewing step for double-sewing a cut periphery of said pad blank to form the figure adjusting pad;

at least one of said molds being formed with a peripheral overflow passage in said mold forming step;

said silicone gel stock solution being poured in said one mold in an amount sufficient to permit said silicone gel stock solution to extend to said peripheral overflow passage and then cured in said peripheral overflow passage as well as in said one mold during said molding forming step;

said pad blank being cut off at a portion thereof corresponding to said peripheral overflow.

7. A process as defined in claim 6, wherein said cutting-off step is carried out so as to leave on said pad blank at least a portion thereof which corresponds in position to said peripheral overflow passage of said mold.

8. A process as defined in claim 6, wherein said cutting-off step is carried out so as to leave on said pad blank no portion thereof which corresponds in position to said peripheral overflow passage of said mold.

9. A process as defined in claim 4, wherein said particles comprise salt and said perforating step is carried out by removing said salt from said silicone gel element by elution using water to provide said silicone gel element with said perforations.

10. A process as defined in claim 7, wherein said particles comprise salt and said perforating step is carried out by removing said salt from said silicone gel element by elution using water to provide said silicone el element with said perforations.

11. A process as defined in claim 8, wherein said particles comprise salt and said perforating step is carried out by removing said slat from said silicone gel element by elution using water to provide said silicone gel element with said perforations 12. A process as defined in claim 6, wherein, in said sewing step, an outer peripheral portion of said pad blank is double-sewn at a predetermined location inwardly of an outermost edge of said pad blank in such a manner as to compress said pad blank at said predetermined location and form an expanded portion outwardly of said predetermined location.

13. A process as defined in claim 12, wherein, further in said sewing step, a trimming fabric element is double-sewn with said pad blank such that said trimming fabric element is wrapped about said outermost edge of said pad blank.

14. A process as defined in claim 12, wherein, in said sewing step, the entire periphery of said pad blank is double-sewn.

15. A process for manufacturing a figure adjusting pad, comprising:

a shaping sheet adhering step for adhering a stretchable fabric and a shaping sheet to each other;

a mold forming step for forming said shaping sheet into two molds;

a pad blank forming step for pouring a silicone gel stock solution having particles incorporated therein into a stretchable fabric side of one of said molds and curing said silicone gel stock solution into a desired shape in a die while heating and pressuring it, to thereby form a pad blank including a cured silicone gel element;

a mold adhering step for adhering a stretchable fabric side of the other of said molds to an exposed surface of said silicone gel element;

a peeling step for peeling only said shaping sheet from each of said molds;

a perforating step for removing said particles from said silicone gel element by elution to provide said silicone gel element with perforations;

a cutting-off step for cutting off an extra peripheral portion of said pad blank therefrom; and a sewing step for double-sewing a periphery of said pad blank to form the figure adjusting pad;

said one mold being formed with a peripheral overflow passage in said mold forming step;

said silicone gel stock solution being poured in said one mold in an amount sufficient to permit said silicone gel stock solution to extend to said peripheral overflow passage and then cured in said peripheral overflow passage as well as in said one mold during said mold forming step;

said pad blank being cut off at a portion thereof corresponding to said peripheral overflow passage.

16. A process as defined in claim 15, wherein said cutting-off step is carried out so as to leave on said pad blank at least a portion thereof which corresponds to said peripheral overflow passage of said mold.

17. A process as defined in claim 15, wherein said cutting-off step is carried out so as to leave on said pad blank no portion thereof which corresponds to said peripheral overflow passage of said mold.

18. A process as defined in claim 15, wherein said particles comprise salt and said perforating step is carried out by removing said salt from said silicone gel element by elution using water to provide said silicone gel element with said perforations.

19. A process as defined in claim 16, wherein said particles comprise salt and said perforating step is carried out by removing said salt from said silicone gel element by elution using water to provide said silicone gel element with said perforations.

20. A process as defined in claim 17, wherein said particles comprise salt and said perforating step is carried out by removing said salt from said silicone gel element by elution using water to provide said silicone gel element with said perforations.

21. A process as defined in claim 15, wherein said sewing step, an outer peripheral portion of said pad blank is double-sewn at a predetermined location inwardly of an outermost edge of said pad blank in such a manner as to compress said pad blank at said predetermined location and form an expanded portion outwardly of said predetermined location.

22. A process as defined in claim 21, wherein, further in said sewing step, a trimming fabric element is double-sewn with said pad blank such that said trimming fabric element is wrapped about said outermost edge of said pad blank.

23. A process as defined in claim 21, wherein, in said sewing step, the entire periphery of said pad blank is double-sewn.

24. A figure adjusting pad comprising;

a silicone gel element having a predetermined shape including an inner portion and an outer peripheral portion about a periphery of said inner portion;

a stretchable fabric covering said silicone gel element in such a manner that an outermost edge of said outer peripheral portion of said silicone gel element is exposed outwardly from said stretchable fabric;

wherein said silicone gel element has perforations formed therein which comprise traces formed by elution of particles incorporated in a silicone gel stock solution for said silicone gel element;

wherein said inner portion of said silicone gel element varies in thickness depending on location;

wherein said stretchable fabric and said outer peripheral portion of said silicon gel element are double-sewn at a predetermined location inwardly of said outermost edge of said outer peripheral portion in such a manner as to compress a portion of said outer peripheral portion of said silicone gel element and form an expanded portion outwardly of said predetermined location, said expanded portion having a thickness less than that of said inner portion of said silicone gel element; and wherein a trimming fabric element is wrapped about the outermost edge of said outer peripheral portion of said silicone el element and about an outermost edge of said stretchable fabric, said trimming fabric element being double-sewn with said stretchable fabric and said outer peripheral portion of said silicone gel element at said predetermined location.

25. A figure adjusting pad as defined in claim 24, wherein said trimming fabric element, said stretchable fabric and said outer peripheral portion of said silicone gel element are double-sewn about an entire periphery of said figure adjusting pad.

26. A figure adjusting pad as defined in claim 24, wherein said stretchable fabric and said outer peripheral portion of said silicone gel element are double-sewn about an entire periphery of said figure adjusting pad.

* * * * *